(12) United States Patent
Ijpeij et al.

(10) Patent No.: US 7,705,172 B2
(45) Date of Patent: Apr. 27, 2010

(54) PROCESS FOR THE PREPARATION OF A METAL-ORGANIC COMPOUND COMPRISING A SPECTATOR LIGAND

(75) Inventors: Edwin Gerard Ijpeij, Sittard (NL); Martin Alexander Zuideveld, Maastricht (NL); Henricus Johannes Arts, Munstergeleen (NL); Francis Van Der Burgt, Herten (NL); Gerardus Henricus Josephus Van Doremaele, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/066,468

(22) PCT Filed: Sep. 13, 2006

(86) PCT No.: PCT/EP2006/008916

§ 371 (c)(1),
(2), (4) Date: Oct. 31, 2008

(87) PCT Pub. No.: WO2007/031295

PCT Pub. Date: Mar. 22, 2007

(65) Prior Publication Data

US 2009/0137830 A1  May 28, 2009

(30) Foreign Application Priority Data

Sep. 16, 2005  (EP) ................. 05077117

(51) Int. Cl.
*C07F 15/06* (2006.01)

(52) U.S. Cl. ..................................... 556/32
(58) Field of Classification Search ............. 556/32
See application file for complete search history.

(56) References Cited

U.S. PATENT DOCUMENTS 6,114,481 A   9/2000  McMeeking et al.

FOREIGN PATENT DOCUMENTS

| WO | 02/070569 | 9/2002 |
|---|---|---|
| WO | 2005/014663 | 2/2005 |
| WO | 2005/014665 | 2/2005 |
| WO | 2005/014666 | 2/2005 |

OTHER PUBLICATIONS

International Search Report for International Application No. PCT/EP2006/008916, mailed Jan. 15, 2007.
Written Opinion of the International Searching Authority, mailed Jan. 15, 2007.

*Primary Examiner*—Porfirio Nazario Gonzalez
(74) *Attorney, Agent, or Firm*—Nixon & Vanderhye P.C.

(57) ABSTRACT

The invention relates to a process for the production of an organometallic compound according to formula (1): $MAL_j Y_r X_{(p-(n+v+r))} R_n$ (formula 1) where: M is a metal of groups 3-13 or the lanthanide series, and p is the valency of the metal M, A represents an anionic spectator ligand whose valency v is 1 or 2, Y is a spectator ligand represented by formula (2): wherein the spectator ligand is covalently bonded to the metal M via the imine nitrogen atom, $Sub_1$ is a substituent, which comprises a group 14 atom through which $Sub_1$ is bonded to the imine carbon atom, $Sub_2$ is a substituent, which comprises an atom of groups 15-16, through which $Sub_2$ is bonded to the imine carbon atom, $sub_1$ and $sub_2$ might be connected to each other forming a ring system, r is an integer>0, L is an optional neutral Lewis basic ligand, j is an integer denoting the number of neutral ligands L, X is an halide, and R is an anionic ligand, wherein an organometallic reagent according to formula (3), $MAL_j X_{p-v}$ (formula 3), is contacted with an alkylating agent, thus forming a precursor in which at least one of the halide atoms is replaced by an anionic ligand R that may be independently selected from the group consisting of alkyl, arylalkyl, aryl, or a combination thereof, which precursor is subsequently contacted with an imine according to formula (2).

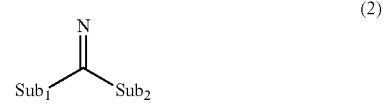

(2)

4 Claims, No Drawings

PROCESS FOR THE PREPARATION OF A METAL-ORGANIC COMPOUND COMPRISING A SPECTATOR LIGAND

This application is the U.S. national phase of International Application No. PCT/EP2006/008916, filed 13 Sep. 2006, which designated the U.S. and claims priority to EP 05077117.9, filed 16 Sep. 2005, the entire contents of each of which are hereby incorporated by reference.

The invention relates to a process for the preparation of an organometallic compound according to formula 1:

$$MAL_jY_rX_{(p-(n+v+r)}R_n \qquad \text{(formula 1)}$$

where:

M is a metal of groups 3-13 or the lanthanide series, and p is the valency of the metal M, A represents an anionic spectator ligand whose valency v is 1 or 2, Y is a spectator ligand represented by formula 2:

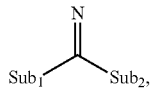

(formula 2)

wherein the spectator ligand is covalently bonded to the metal M via the imine nitrogen atom, $Sub_1$ is a substituent, which comprises a group 14 atom through which $Sub_1$ is bonded to the imine carbon atom. $Sub_2$ is a substituent, which comprises an atom of groups 15-16, through which $Sub_2$ is bonded to the imine carbon atom, $Sub_1$ and $Sub_2$ may be connected to each other to form a ring system, r is an integer>0 and represents the number of spectator ligands Y, L is an optional neutral Lewis basic ligand, and j is an integer denoting the number of neutral ligands L, X is a halide, and R is an anionic ligand. Organometallic compounds thus produced are typically used as precatalyst in the production of polyolefins.

Such a process is known from WO-A1-2005/014663. WO-A1-2005/014663 describes a process for the preparation of an organometallic compound comprising an imine ligand. Imine ligands for these precatalysts can be guanidine, iminoimidazoline, amidine or a ketimine.

In this process $CpTiCl_3$ is reacted with the imine ligand and the reaction product, being an intermediate dichloride complex, is subsequently alkylated with an organolithium compound or an organomagnesium compound.

In both steps side products are formed which have to be removed. This is typically done by filtration. To obtain an acceptable yield, the organometallic compound has to be extracted one or more times from the side products. In the known process the reaction and extraction solvent is typically toluene. Toluene however is an undesired compound in the subsequent polymerization process and therefore has to be removed from the organometallic compound. An additional disadvantage of toluene is the fact that it is difficult to remove from the prepared organometallic compound, and from a polyolefin prepared with a toluene-comprising organometallic compound.

It is therefore desired to carry out the process for the preparation of the organometallic compound in an aliphatic solvent. However, as the solubility of the intermediate dichloride complex is low in aliphatic solvents, a significant amount of solvent has to be used to extract this product from the side products. Furthermore, the reaction between $CpTiCl_3$ and the imine ligand is very slow in an aliphatic solvent.

An object of the present invention is therefore to provide an alternative process for the preparation of an organometallic compound that can be carried out in an aliphatic hydrocarbon without the above-mentioned disadvantages.

According to the invention this is obtained by the process as described in claim 1.

With the method of the invention an organometallic compound, suitable as precatalyst in olefin polymerization, can be prepared in an aliphatic hydrocarbon (linear, branched or cyclic) comprising between 3 and 20 carbon atoms, which is generally the same solvent as is used in a subsequent olefin polymerization. An additional advantage of the method of the invention is that during the second step of the process, wherein the precursor is contacted with the spectator ligand, no solid side products are formed, so that purification after this step is not necessary before the precatalyst prepared according to the method of the invention can be applied in a subsequent olefin polymerization process. The organometallic compound prepared by the method of the invention has the same performance as an organometallic compound prepared via known production processes. Another advantage of this method is that multiple extractions and solvent changes, through evaporation of the reaction or extraction solvent and then by being redissolved in a solvent suitable for the polymerization, can be avoided. A further advantage of the process of the invention is that the process can be carried out at room temperature.

In the process of the invention a metal organic reagent according to formula 3, $$MAL_jX_{p-v} \qquad \text{(formula 3),}$$

is contacted with an alkylating agent, thus forming a precursor in which at least one of the halide atoms is replaced by an anionic ligand R.

M is a metal of groups 3-13 or the lanthanide series, and p is the valency of the metal M.

The ligand L may be present in the organometallic compound for reasons of stability. If the ligand L is present, L can be an ether, a thioether, a tertiary amine, a tertiary phosphane, an imine, or a bi-, or oligodentate, comprising an ether, a thioether, a tertiary amine, or a tertiary phosphane functional group, or combinations thereof.

A represents an anionic spectator ligand whose valency v is 1 or 2. Suitable ligands A are (substituted) cyclopentadienyl groups, (substituted) indenyl groups, (substituted) fluorenyl groups, (substituted) tetrahydroindenyl groups, (substituted) tetrahydrofluorenyl groups, (substituted) octahydrofluorenyl groups, (substituted) benzoindenyl groups, (substituted) heterocyclopentadienyl groups, (substituted) heteroindenyl groups, (substituted) heterofluorenyl groups, or their isomers. A heterocyclopentadienyl group (hereinafter referred to as 'hetero ligand') is understood to be a group that has been derived from a cyclopentadienyl group, but in which at least one of the C atoms in the 5-ring of the cyclopentadienyl has been replaced by a heteroatom, which heteroatom may be chosen from group 13, 15 or 16. If there is more than one heteroatom present in the 5-ring of the hetero ligand, these heteroatoms may be the same or different. More preferably, the heteroatom is chosen from group 15, while yet more preferably the heteroatom is phosphorus.

R is an anionic ligand independently selected from the group consisting of alkyl or arylalkyl, e.g. benzyl, aryl, or a combination thereof. Preferably, the anionic ligand R is free from β-hydrogen atoms on an aliphatic carbon atom.

Examples of anionic ligands free from β-hydrogen atoms are methyl, and compounds with the general formula —CH$_2$—(BR$_1$R$_2$R$_3$), wherein B can be C, Si or Ge, and the substituents R$_1$, R$_2$ and R$_3$ can be chosen from the group of (cyclo) aliphatic hydrocarbons, or (substituted) aromatic hydrocarbons. R$_1$, R$_2$ and R$_3$ can be the same or different, both substituted and unsubstituted. R is preferably methyl or benzyl.

The spectator ligand Y, represented by formula 2 is covalently bonded to the metal via the imine nitrogen atom. Sub$_1$ is a substituent that comprises a group 14 atom, preferably a carbon atom through which Sub$_1$ is bound to the imine carbon atom. Sub$_1$ preferably represents a hydrocarbyl radical, optionally substituted with heteroatoms of groups 13-17, or a silyl radical, optionally substituted with group 13-17 atoms.

Sub$_2$ is a substituent, which comprises an atom of groups 15-16, through which Sub$_2$ is bonded to the imine carbon atom. Preferably, this atom is selected from the group of nitrogen, phosphorus, oxygen or sulfur. Sub$_2$ is preferably an amide, imide, phosphide, phospinimide, oxide, sulphide radical, optionally substituted with hydrocarbyl radicals or silyl radicals as described for Sub$_1$.

An organometallic compound according to the invention exhibits a high efficiency for the polymerization of both ethylene and propylene or copolymers of ethylene and alpha olefins and terpolymers of ethylene, alpha olefins and other polymerizable olefins having one or more double bonds. Catalysts comprising the organometallic compound according to the invention are particularly suitable for the production of EPDM.

The process of the invention is carried out in an aliphatic hydrocarbon with between 3 and 20 carbon atoms. Examples of suitable hydrocarbons are isobutane, pentane, isopentane, hexane, cyclohexane, heptane, cycloheptane.

The invention will be elucidated with some non-limiting examples:

Part 1: Synthesis of Catalyst Components

General Part

Experiments were performed under a dry and oxygen-free nitrogen atmosphere using Schlenk-line techniques. $^1$H-NMR, $^{13}$C-NMR-spectra and $^{19}$F-NMR-spectra were measured on a Bruker Avance 300 spectrometer. Aliphatic solvents were distilled from sodium/potassium alloy with benzophenone as indicator. Me5CpTiMe3 was prepared as mentioned in: *Organometallics*, 8 (1989), 376-382. Other starting materials were used as obtained.

Synthesis of
N,N-diisopropyl-2,6-difluoro-benzamidine
(Ligand 1)

A solution of EtMgBr in ether (8.0 ml, 3.0 M, 23 mmol) was added to a solution of diisopropylamine (2.5 g, 23.8 mmol) in toluene (60 ml) at 50° C. The mixture was stirred for 1 h and a white precipitate formed. The mixture was cooled to 0° C. and 2,6-difluorobenzonitrile (3.33 g, 23 mmol) was added. The mixture was allowed to warm to room temperature and stirred for 16 hours subsequently. The conversion, determined by GC, appeared to be 98%. The mixture was quenched with an aqueous solution of ammonium chloride (10%, 100 ml). The organic phase was separated from the aqueous phase and the latter was extracted twice with diethylether (200 ml). The combined organic phases were dried over sodium sulphate, filtered and the solvent was removed under reduced pressure giving 5.30 g (91%) of pure product.

The ligand was characterized by $^1$H NMR 300 MHz (CDCl$_3$) δ (ppm): 7.2 (m, 1H), 6.8 (m. 2H), 5.5 (bs, 1H), 3.7 (bs, 1H), 1.5 (bs, 6H), 1.0 (bs 6H), by $^{13}$C NMR 75 MHz (CDCl$_3$) δ (ppm): 158.9 dd, J=238 Hz, J=8 Hz), 155.7, 130.1, v130.0, 129.8, 112.1, 112.0, 111.9, 111.8, 52.0 (bs), 36.2 (bs), 21.3, 20.5 and by $^{19}$F NMR 282 MHz (CDCl$_3$) δ (ppm): −113.5

COMPARATIVE EXPERIMENT A

Conventional Synthesis of Me$_5$CpTi(Me$_2$)(NC(2,6-F$_2$Ph)($^i$Pr$_2$N)) (Compound 1) in Toluene Me$_5$CpTiCl$_3$ (7.23 g, 25 mmol) and N,N-diisopropyl-2,6-difluorobenzamidine (6.05 g, 25.2 mmol) were dissolved in toluene (150 ml). Next triethylamine (3.0 ml, 2.9 g, 29 mmol) was added and the reaction mixture was stirred for 18 hours. The reaction mixture was filtered and the residue was rinsed once with toluene (60 ml). The toluene of the combined organic phases (filtrate and rinse liquid) was removed in vacuo. The residue was triturated with hexane (60 ml) resulting in 12.18 g (99%) of Me$_5$CpTiCl$_2$(NC(2,6-F$_2$Ph)($^i$Pr$_2$N)) as an orange powder. The product was characterized by $^1$H NMR 300 MHz (CDCl$_3$) δ (ppm): 7.2 (pent, 1H), 6.9 (dd, 2H), 3.8 (bs, 1H), 3.6 (sept, 1H), 2.0 (s, 15H), 1.5 (d, 6H), 1.1 (d, 6H), and by $^{13}$CNMR 75MHz (CDCl$_3$) δ (ppm): 157.1 (dd, J=250 Hz and J=8 Hz), 152.3, 129.3, (t, J=10 Hz), 126.3, 113.6 (t, J=23 Hz), 110.8 (m), 51.3 (bs), 37.3, 19.5, 19.3, 12.0

To a solution of Me$_5$CpTiCl$_2$(NC(2,6-F$_2$Ph)($^i$Pr$_2$N)) (12.18 g, 23.7 mmol) in toluene (100 ml) was added a solution of methylmagnesiumbromide (16.5 ml, 3.0 M in diethylether, 39.5 mmol) at −78° C. The reaction mixture was stirred at room temperature for 18 hours. The reaction mixture was filtered and the solvent was removed in vacuo. The residue was triturated with hexane (100 ml) resulting in 10.9 g of product as a yellow powder (97%). The product was characterized by $^1$H NMR 300 MHz (CDCl$_3$) δ (ppm): 7.8 (d pent, 1H), 7.0 (dd, 2H), 3.0 (bs, 1H), 3.8 (sept, 1H), 1.9 (s, 15H), 1.8 (d, 6H), 1.3 (d, 6H), 0.0 (s, 6H), by $^{13}$C NMR 75 MHz (CDCl$_3$) δ (ppm): 153.7 (dd, J=238 Hz and J=8 Hz), 136.5, 127.1, (t, J=10 Hz), 118.7, 117.2 (t, J=25 Hz), 110.3 (m), 50.5, 37.1, 20.1, 19.3, 10.3 and by $^{19}$F NMR 282 MHz (CDCl$_3$) δ (ppm): −113.3

COMPARATIVE EXPERIMENT B1

Conventional Synthesis of Me$_5$CpTi(Cl$_2$)(NC(2,6-F$_2$Ph)($^i$Pr$_2$N)) (Compound 1) in Aliphatic Solvents Me$_5$CpTiCl$_3$ (580 mg, 2.00 mmol) and N,N-diisopropyl-2,6-difluorobenzamidine (482 mg, 2.01 mmol) were dissolved in hexane (30 ml). Only a small amount of the Me$_5$CpTiCl$_3$ dissolved. Next triethylamine (0.5 ml) was added and the reaction mixture was stirred for 18 hours. The reaction mixture was filtered and the residue was rinsed once with hexanes (30 ml). The hexane of the combined organic phases (filtrate and rinse liquid) was removed in vacuo resulting in 0.44 g of products as an orange powder. The product consisted of a mixture of the desired complex, contaminated with unreacted Me$_5$CpTiCl$_3$ and N,N-diisopropyl-2,6-difluorobenzamidine as can be concluded from NMR analysis. $^1$H NMR 300 MHz (CDCl$_3$) δ (ppm): 7.2 (pent, 1H), 6.9 (dd, 2H), 3.8 (bs, 1H), 3.6 (sept, 1H), 2.3 (s, unreacted Me5CpTiCl3), 2.0 (s, 15H), 1.5 (d, 9H), 1.1 (d, 9H).

COMPARATIVE EXPERIMENT B2

Conventional Synthesis of $Me_5CpTi(Cl_2)(NC(2,6-F_2Ph)(^iPr_2N))$ (Compound 1) in Aliphatic Solvents $Me_5CpTiCl_3$ (580 mg, 2.00 mmol) and N,N-diisopropyl-2,6-difluorobenzamidine (488 mg, 2.03 mmol) were dissolved in hexanes (30 ml). Only a small amount of the $Me_5CpTiCl_3$ dissolved. Next triethylamine (0.5 ml) was added and the reaction mixture was stirred for 60 hours. The reaction mixture was filtered and the residue was rinsed once with hexanes (50 ml). The solvent of the combined organic phases (filtrate and rinse liquid) was removed in vacuo resulting in 0.33 g (33%) of products as an orange powder. The product was characterized by $^1H$ NMR 300 MHz ($CDCl_3$) δ (ppm): 7.2 (pent, 1H), 6.9 (dd, 2H), 3.8 (bs, 1H), 3.6 (sept, 1H), 2.0 (s, 15H), 1.5 (d, 6H), 1.1 (d, 6H). Although the resulting product was not contaminated with unreacted $Me_5CpTiCl_3$ and N,N-diisopropyl-2,6-difluorobenzamidine, the yield after a much longer reaction time (60 hours instead of the 18 hours in Comparative Experiment 1) and the use of more liquid for rinsing (50 ml versus 30 ml) was only 33%.

EXAMPLE 1

Synthesis of $Me_5CpTi(Me_2)(NC(2,6-F_2Ph)(^iPr_2N))$ (Compound 1) Synthesis of pentamethylcyclopentadienyltitaniumtrimethyl Pentamethylcyclopentadienyltitaniumtrichloride (3.09 g, 10.7 mmol) were suspended in hexane (50 ml). The suspension was cooled to 0° C. and methyllithium solution (1.6M in diethylether, 20.0 ml, 32 mmol) was added dropwise. The mixture was stirred at 0° C. for 2½ hours after which it was allowed to warm to room temperature. Stirring was continued at room temperature for 30 minutes. The solids were filtered off and washed once with hexanes (30 ml). The combined hexane solutions of filtrate and rinse liquid were evaporated to dryness resulting in 2.37 g (98%) of light brown product. The product was characterized by $^1H$ NMR 300 MHz ($CDCl_3$) δ (ppm): 1.9 (s, 15H), 0.7 (s, 9H).

Method a) $Me_5CpTiMe_3$ (1.17 g, 5.1 mmol) and 1.23 g of N,N-diisopropyl-2,6-difluoro-benzamidine (5.1 mmol) were dissolved in a mixture of hexanes (ligroin, 30 ml). The reaction mixture was stirred for 18 hours at room temperature. The solvent was removed in vacuo resulting in 2.21 g of a light brown powder (95%). The product was characterized by $^1H$ NMR 300 MHz ($CDCl_3$) δ (ppm): 7.3 (d pent, 1H), 7.0 (dd, 2H), 4.0 (bs, 1H), 3.8 (sept, 1H), 1.9 (s, 15H), 1.8 (d, 6H), 1.3 (d, 6H), 0.0 (s, 6H).

Method b) $Me_5CpTiMe_3$ (230 mg, 1.01 mmol) and N,N-diisopropyl-2,6-difluoro-benzamidine (232 mg, 1.01 mmol) were dissolved in hexanes (30 ml). After 2, 4 and 24 hours aliquots of 3 ml were taken from the reaction mixture and diluted to 100 ml with hexanes. The diluted solutions were used in polymerization experiments. In table 1 they are indicated as compound ½, ¼ and 1/24, depending on the time they were taken from the solution.

Synthesis of N,N-dicyclohexylbenzamidine (Ligand 2)

Dicyclohexylamine (18.1 g, 0.10 mmol) was dissolved in diethylether (150 ml). The solution was heated to reflux temperature and a solution of methylmagnesiumbromide (33 ml, 3.0 M in diethylether, 0.10 mol) was added dropwise over a period of 20 minutes. After the addition, the reaction mixture was stirred for 3 hours at room temperature. Benzonitrile (10.3 g, 0.10 mol) was added and the reaction mixture was stirred for 20 hours at room temperature. A solution of ammoniumchloride (10% in water, 100 ml) was added. The water and organic layers were separated and the water layer was extracted twice with diethylether (150 ml). The combined ether layers were dried over sodium sulphate, filtered and the solvent was evaporated from the filtrate resulting in a yellow wax (23.6 g). The product was further purified by short path distillation (kugelrohr, P=0.8 mbar, T=150° C.). Yield 19.5 g (69%). The product was characterized by $^1H$ NMR 300 MHz ($CDCl_3$) δ (ppm): 7.3 (dd, 3H), 7.2 (dd, 2H), 5.7 (bs, 1H), 3.1 (tt, 2H), 2.0 (bq, 3H), 1.7 (m, 8H), 1.5 (d, 2H), 1.1 (m, 6H) and by $^{13}C$ NMR 75 MHz ($CDCl_3$) δ (ppm): 169.3, 131.9, 128.7, 128.3, 126.2, 58.6, 31.6, 27.0, 25.8

EXAMPLE 2

Synthesis of $Me_5CpTi(Me_2)(NC(Ph)(NCy_2))$ (Compound 2)

$Me_5CpTiMe_3$ (227 mg, 1.00 mmol) and N,N-dicyclohexylbenzamidine[13] (281 mg, 0.99 mmol) are dissolved in hexanes (30 ml). After 2, 4 and 24 hours aliquots of 3 ml were taken from the reaction mixture and diluted to 100 ml with hexanes. The diluted solutions were used in polymerization experiments.

Part II: Batch EPDM Terpolymerizations (General Procedure)

In an inert atmosphere of nitrogen, the reactor was filled with pentamethylheptane (PMH) (950 mL), MAO (Crompton, 10 wt % in toluene), butylated hydroxytoluene (BHT), 5-ethylidene-2-norbornene (ENB) (0.7 mL) and 5-vinyl-2-norbornene (VNB) (0.7 mL). The reactor was heated to 90° C., while stirring at 1350 rpm. The reactor was pressurized and conditioned under a determined ratio of ethylene, propylene and hydrogen (0.35 NL/h) After 15 minutes, the catalyst components were added into the reactor and the catalyst vessel was rinsed with PMH (50 mL) subsequently. After 10 minutes of polymerization, the monomer flow was stopped and the solution was carefully dumped in an Erlenmeyer flask of 2 L, containing a solution of Irganox-1076 in isopropanol and dried overnight at 100° C. under reduced pressure. The polymers were analyzed using FT-IR for composition and SEC-DV for the molecular weight distribution.

Polymer Analysis

The polymers that were prepared as described in the examples were analyzed by means of Size Exclusion Chromatography (SEC) coupled with Refractive Index (RI) and Differential Viscometry (DV) detection.

The equipment and the experimental conditions for the so-called SEC-DV analysis were as follows:

| | |
|---|---|
| Equipment: | PL220 (Polymer Laboratories) SEC with PL220 DRI concentration detector and PL-BV 400 viscometry detector. Detectors are operated in parallel configuration. PL solvent degasser PL-DG802 |
| Data processing: | Viscotek data processing software, TriSEC 2.7 or higher version |
| Columns: | Tosoh Bioscience (TSK) GMHHR-H(S) HT mixed bed (4x) |
| Calibration: | Universal calibration with linear polyethylene (PE) standard (molecular weight 0.3-3000 kg/mol) |

-continued

| | |
|---|---|
| Temperature: | 140° C. |
| Flow: | 1.0 ml/min |
| Injection volume: | 0.300 ml |
| Solvent/eluent: | Distilled 1,2,4-trichlorobenzene with about 1 g/l of Ionol stabilizer |
| Sample preparation: | Dissolving for 4 hours at approx. 150° C. Filtration through 1.0 micron regenerated cellulose filter Sample concentration approx. 1.0 mg/ml |

By means of Fourier transformation infrared spectroscopy (FT-IR), the composition of the copolymers was determined according to the method that is customary in the rubber industry. The FT-IR measurement gives the composition of the various monomers in weight percent relative to the total composition.

COMPARATIVE POLYMERIZATION EXAMPLE A

Terpolymerization was carried out according to the procedure as described above, with Compound 1 prepared according to the method in comparative example A. The results are given in table 1.

POLYMERIZATION EXAMPLES 1-3

Terpolymerization was carried out according to the procedure as described above, with Compound 1 prepared according to method b, with time intervals mentioned as in the preparation. The results are given in table 1.

POLYMERIZATION EXAMPLES 3-6

Terpolymerization was carried out according to the procedure as described above, with Compound 2 prepared with time intervals mentioned as in the preparation. The results are given in table 1.

The invention claimed is:

1. A process for the production of an organometallic compound according to formula 1:

$$MAL_jY_rX_{(p-(n+v+r)}R_n \quad \text{(formula 1)}$$

where:

M is a metal of groups 3-13 or the lanthanide series, and p is the valence of the metal M, A represents an anionic spectator ligand whose valence v is 1 or 2, Y is a spectator ligand represented by formula 2:

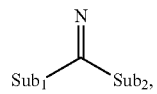

(formula 2)

wherein the spectator ligand is covalently bonded to the metal M via the imine nitrogen atom, $Sub_1$ is a substituent, which comprises a group 14 atom through which $Sub_1$ is bonded to the imine carbon atom, $Sub_2$ is a substituent, which comprises an atom of groups 15-16, through which $Sub_2$ is bonded to the imine carbon atom, $Sub_1$ and $Sub_2$ might be connected to each other forming a ring system, r is an integer >0, n is the number of anionic ligands R, L is an optional neutral Lewis basic ligand, j is an integer denoting the number of neutral ligands L, X is a halide, and R is an anionic ligand, wherein an organometallic reagent according to formula 3, $$MAL_jX_{p-v} \quad \text{(formula 3)},$$

is contacted with an alkylating agent, thus forming a precursor in which at least one of the halide atoms is replaced by an anionic ligand R that may be independently selected from the group consisting of alkyl,

| Example | Organo-metallic compound/ Reaction time (Hrs) | Activator system | Al/Ti Molar ratio | BHT/ Al Molar ratio | Organo-metallic compound dosage (µmol) | C3⁻ feed to reactor (NL/h) | C2⁻ feed to reactor (NL/h) | ΔT (° C.) |
|---|---|---|---|---|---|---|---|---|
| A | 1 | MAO | 9000 | 2 | 0.05 | 400 | 200 | 1.5 |
| 1 | 1/2 | MAO | 3000 | 2 | 0.15 | 250 | 250 | 1.8 |
| 2 | 1/4 | MAO | 6300 | 2 | 0.07 | 250 | 250 | 2.3 |
| 3 | 1/24 | MAO | 6300 | 2 | 0.07 | 250 | 250 | 2.7 |
| 3 | 2/2 | MAO | 6300 | 2 | 0.07 | 250 | 250 | 1.2 |
| 5 | 2/4 | MAO | 6300 | 2 | 0.07 | 250 | 250 | 1.6 |
| 6 | 2/24 | MAO | 6300 | 2 | 0.07 | 250 | 250 | 1.8 |

| Example | Yield (g) | Residual Ti in polymer (ppm) | Incorporated C3⁻ (wt %) | ENB (wt %) | VNB (wt %) | Mw (kg/mol) | Mz (kg/mol) | Mw/Mn |
|---|---|---|---|---|---|---|---|---|
| A | 6.8 | 0.4 | 53.9 | 1.0 | 0.7 | nd | nd | Nd |
| 1 | 5.8 | 1.2 | 31.8 | 1.1 | 0.8 | | | |
| 2 | 6.8 | 0.5 | 31.8 | 1.2 | 0.8 | | | |
| 3 | 7.6 | 0.3 | 30.8 | 1.2 | 0.8 | 310 | 690 | 2.3 |
| 3 | 3.5 | 0.8 | 30.0 | 1.2 | 0.7 | 320 | 700 | 2.3 |
| 5 | 5.6 | 0.6 | nd | nd | nd | nd | nd | Nd |
| 6 | 5.2 | 0.6 | 31.3 | 1.3 | 0.7 | 290 | 680 | 2.8 | arylalkyl, aryl, or a combination thereof, which precursor is subsequently contacted with an imine according to formula 2 in an aliphatic hydrocarbon solvent comprising between 3 and 20 carbon atoms.

2. The process as claimed in claim 1, wherein the anionic ligand R is free from β-hydrogen atoms on an aliphatic carbon atom.

3. The process as claimed in claim 1, wherein the anionic ligand R is methyl or benzyl.

4. The process as claimed in claim 1, wherein the aliphatic hydrocarbon is isobutane, pentane, isopentane, hexane, cyclohexane, heptane, or cycloheptane.

* * * * *